United States Patent
Donofrio et al.

(12)

(10) Patent No.: US 7,993,269 B2
(45) Date of Patent: Aug. 9, 2011

(54) SENSOR AND METHOD FOR SPINAL MONITORING

(75) Inventors: William T. Donofrio, Andover, MN (US); Jeffrey H. Nycz, Collierville, TN (US); Steven Tethrake, Collierville, TN (US); Stanley Warren Olson, Jr., Germantown, TN (US)

(73) Assignee: Medtronic, Inc., Minneapolis, MN (US)

( * ) Notice: Subject to any disclaimer, the term of this patent is extended or adjusted under 35 U.S.C. 154(b) by 1575 days.

(21) Appl. No.: 11/356,687

(22) Filed: Feb. 17, 2006

(65) Prior Publication Data

US 2007/0232958 A1    Oct. 4, 2007

(51) Int. Cl.
*A61B 5/00*    (2006.01)
*A61B 5/103*    (2006.01)

(52) U.S. Cl. ............... 600/309; 600/594; 128/903

(58) Field of Classification Search .......... 600/309–310, 600/316, 345, 361, 363, 437, 473, 475, 561, 600/587, 594–595
See application file for complete search history.

(56) References Cited

U.S. PATENT DOCUMENTS

| | | | |
|---|---|---|---|
| 3,181,528 A | | 5/1965 | Brackin |
| 4,195,367 A | * | 4/1980 | Kraus |
| 4,195,643 A | | 4/1980 | Pratt, Jr. |
| 4,246,791 A | | 1/1981 | Glenn |
| 4,430,999 A | * | 2/1984 | Brighton et al. |
| 4,519,394 A | * | 5/1985 | Black et al. |
| 4,669,482 A | | 6/1987 | Ophir |
| 4,672,963 A | * | 6/1987 | Barken |
| 4,781,181 A | | 11/1988 | Tanguy |
| 4,813,435 A | | 3/1989 | Arms |
| 4,993,428 A | | 2/1991 | Arms |
| 5,038,787 A | | 8/1991 | Antich et al. |
| 5,078,140 A | * | 1/1992 | Kwoh .................. 600/417 |
| 5,083,573 A | | 1/1992 | Arms |
| 5,125,408 A | | 6/1992 | Basser |
| 5,178,148 A | * | 1/1993 | Lacoste et al. |
| 5,197,475 A | | 3/1993 | Antich et al. |
| 5,197,488 A | | 3/1993 | Kovacevic |
| 5,289,826 A | | 3/1994 | Kovacevic |
| 5,306,306 A | | 4/1994 | Bisek et al. |
| 5,360,016 A | | 11/1994 | Kovacevic |
| 5,394,875 A | * | 3/1995 | Lewis et al. |
| 5,402,781 A | | 4/1995 | Dimaragonas |
| 5,413,116 A | | 5/1995 | Radke et al. |
| 5,425,775 A | | 6/1995 | Kovacevic et al. |
| 5,456,724 A | | 10/1995 | Yen et al. |
| 5,470,354 A | | 11/1995 | Hershberger et al. |

(Continued)

FOREIGN PATENT DOCUMENTS

DE    10342823 A1    5/2007

(Continued)

OTHER PUBLICATIONS

U.S. Appl. No. 11/344,667, filed Feb. 1, 2006 in the name of Donofrio, et al.

(Continued)

*Primary Examiner* — Francis Jaworski (57) ABSTRACT

A sensor for detecting changes in spinal tissue is disclosed. The implantable sensor or surgical instrument includes a sensing element adapted for detecting indicators of tissue health. The sensor is configured for transmitting the tissue data outside of the body. Further a system and method are provided to utilize the sensed tissue properties to treat the patient's condition.

19 Claims, 5 Drawing Sheets

U.S. PATENT DOCUMENTS

| | | | |
|---|---|---|---|
| 5,480,439 A | 1/1996 | Bisek et al. | |
| 5,533,519 A | 7/1996 | Radke et al. | |
| 5,564,423 A | 10/1996 | Mele et al. | |
| 5,590,658 A | 1/1997 | Chiang et al. | |
| 5,610,966 A | 3/1997 | Martell et al. | |
| 5,690,114 A | 11/1997 | Chiang et al. | |
| 5,694,946 A | 12/1997 | Tenerz et al. | |
| 5,695,496 A | 12/1997 | Orsak et al. | |
| 5,749,363 A | 5/1998 | Ishii et al. | |
| 5,810,735 A | 9/1998 | Halperin et al. | |
| 5,836,876 A | 11/1998 | Dimarogonas | |
| 5,839,442 A | 11/1998 | Chiang et al. | |
| 5,852,647 A | 12/1998 | Schick et al. | |
| 5,853,005 A | 12/1998 | Scanlon et al. | |
| 5,891,033 A | 4/1999 | O'Neill et al. | |
| 5,935,171 A | 8/1999 | Schneider et al. | |
| 5,957,846 A | 9/1999 | Chiang et al. | |
| 5,964,709 A | 10/1999 | Chiang et al. | |
| 6,034,296 A | 3/2000 | Elvin et al. | |
| 6,059,784 A | 5/2000 | Perusek | |
| 6,074,394 A | 6/2000 | Krause | |
| 6,106,472 A | 8/2000 | Chiang et al. | |
| 6,200,266 B1 | 3/2001 | Shokrollahi et al. | |
| 6,230,036 B1 | 5/2001 | O'Neill et al. | |
| 6,235,038 B1 | 5/2001 | Hunter et al. | |
| 6,241,673 B1 | 6/2001 | Williams et al. | |
| 6,245,109 B1 | 6/2001 | Mendes et al. | |
| 6,292,680 B1 | 9/2001 | Somogyi et al. | |
| 6,364,849 B1 | 4/2002 | Wilcox | |
| 6,370,420 B1 * | 4/2002 | Kraft | 600/431 |
| 6,433,629 B2 | 8/2002 | Hamel et al. | |
| 6,436,042 B1 | 8/2002 | Cadossi et al. | |
| 6,447,448 B1 | 9/2002 | Ishikawa et al. | |
| 6,497,672 B2 | 12/2002 | Kramer | |
| 6,503,249 B1 | 1/2003 | Krause | |
| 6,529,127 B2 | 3/2003 | Townsend et al. | |
| 6,537,233 B1 | 3/2003 | Rangayyan et al. | |
| 6,540,685 B1 | 4/2003 | Rhoads et al. | |
| 6,544,749 B1 | 4/2003 | Kim | |
| 6,558,390 B2 * | 5/2003 | Cragg | 606/80 |
| 6,573,706 B2 | 6/2003 | Mendes et al. | |
| 6,583,630 B2 | 6/2003 | Mendes et al. | |
| 6,585,647 B1 | 7/2003 | Winder | |
| 6,610,096 B2 | 8/2003 | MacDonald | |
| 6,610,101 B2 | 8/2003 | Herr et al. | |
| 6,621,278 B2 | 9/2003 | Ariav | |
| 6,628,989 B1 | 9/2003 | Penner et al. | |
| 6,656,135 B2 | 12/2003 | Zogbi et al. | |
| 6,676,291 B2 | 1/2004 | Ahn | |
| 6,692,450 B1 | 2/2004 | Coleman | |
| 6,695,885 B2 | 2/2004 | Schulman et al. | |
| 6,706,005 B2 | 3/2004 | Roy et al. | |
| 6,706,071 B1 | 3/2004 | Wolter | |
| 6,719,692 B2 * | 4/2004 | Kleffner et al. | 600/437 |
| 6,733,458 B1 * | 5/2004 | Steins | |
| 6,761,741 B2 | 7/2004 | Iesaka | |
| 6,821,299 B2 | 11/2004 | Kirking et al. | |
| 6,849,463 B2 | 2/2005 | Santini et al. | |
| 6,856,141 B2 | 2/2005 | Ariav | |
| 6,889,165 B2 | 5/2005 | Lind et al. | |
| 6,899,680 B2 | 5/2005 | Hoff et al. | |
| 6,918,308 B2 | 7/2005 | Biedermann et al. | |
| 6,980,419 B2 | 12/2005 | Smith et al. | |
| 6,984,993 B2 | 1/2006 | Ariav | |
| 7,097,662 B2 * | 8/2006 | Evans et al. | 623/18.11 |
| 7,449,019 B2 * | 11/2008 | Uchida et al. | 606/27 |
| 7,452,351 B2 * | 11/2008 | Miller et al. | 604/506 |
| 7,531,002 B2 * | 5/2009 | Sutton et al. | 623/17.15 |
| 7,627,380 B2 * | 12/2009 | Podhajsky et al. | 607/99 |
| 7,766,961 B2 * | 8/2010 | Patel et al. | 623/1.35 |
| 2002/0024450 A1 | 2/2002 | Townsend et al. | |
| 2002/0049394 A1 | 4/2002 | Roy et al. | |
| 2002/0103435 A1 | 8/2002 | Mault | |
| 2002/0107649 A1 | 8/2002 | Takiguchi et al. | |
| 2002/0133094 A1 | 9/2002 | Wilcox et al. | |
| 2002/0198526 A1 | 12/2002 | Shaolian et al. | |
| 2003/0069644 A1 | 4/2003 | Kovacevic et al. | |
| 2003/0120150 A1 | 6/2003 | Govari | |
| 2003/0139690 A1 | 7/2003 | Aebli et al. | |
| 2003/0167002 A1 | 9/2003 | Nagar et al. | |
| 2003/0199783 A1 | 10/2003 | Bloom et al. | |
| 2004/0011137 A1 | 1/2004 | Hnat et al. | |
| 2004/0021322 A1 | 2/2004 | Ariav | |
| 2004/0054302 A1 | 3/2004 | Czernicki | |
| 2004/0059423 A1 | 3/2004 | Barnes et al. | |
| 2004/0068205 A1 | 4/2004 | Zogbi et al. | |
| 2004/0113790 A1 | 6/2004 | Hamel et al. | |
| 2004/0129095 A1 | 7/2004 | Churchill et al. | |
| 2004/0143186 A1 | 7/2004 | Anisimov et al. | |
| 2004/0143302 A1 | 7/2004 | Sieracki | |
| 2004/0152972 A1 * | 8/2004 | Hunter | 600/424 |
| 2004/0186396 A1 | 9/2004 | Roy et al. | |
| 2004/0204647 A1 | 10/2004 | Grupp et al. | |
| 2004/0204744 A1 | 10/2004 | Penner et al. | |
| 2004/0207409 A1 | 10/2004 | Ariav et al. | |
| 2004/0236192 A1 | 11/2004 | Necola | |
| 2004/0236221 A1 | 11/2004 | Wilcox et al. | |
| 2005/0010299 A1 | 1/2005 | Disilvestro | |
| 2005/0010300 A1 | 1/2005 | Disilvestro et al. | |
| 2005/0010301 A1 | 1/2005 | Disilvestro et al. | |
| 2005/0010302 A1 | 1/2005 | Dietz et al. | |
| 2005/0012610 A1 | 1/2005 | Liao et al. | |
| 2005/0012617 A1 | 1/2005 | DiSilvestro et al. | |
| 2005/0015010 A1 | 1/2005 | Antich et al. | |
| 2005/0027192 A1 | 2/2005 | Govari et al. | |
| 2005/0085725 A1 | 4/2005 | Nagar et al. | |
| 2005/0099290 A1 | 5/2005 | Govari | |
| 2005/0113691 A1 | 5/2005 | Liebschner | |
| 2005/0119587 A1 | 6/2005 | Roessler et al. | |
| 2005/0124896 A1 * | 6/2005 | Richter et al. | 600/458 |
| 2005/0165317 A1 | 7/2005 | Turner et al. | |
| 2005/0197576 A1 | 9/2005 | Luo et al. | |
| 2005/0234555 A1 | 10/2005 | Sutton et al. | |
| 2005/0245821 A1 | 11/2005 | Govari et al. | |
| 2005/0272990 A1 | 12/2005 | Ariav et al. | |
| 2005/0273170 A1 | 12/2005 | Navarro et al. | |
| 2005/0288596 A1 | 12/2005 | Eigler et al. | |
| 2005/0288604 A1 | 12/2005 | Eigler et al. | |
| 2005/0288722 A1 | 12/2005 | Eigler et al. | |
| 2006/0009856 A1 | 1/2006 | Sherman et al. | |
| 2006/0030914 A1 | 2/2006 | Eggers et al. | |
| 2006/0032314 A1 | 2/2006 | Hnat et al. | |
| 2006/0036246 A1 | 2/2006 | Carl et al. | |
| 2006/0036256 A1 | 2/2006 | Carl et al. | |
| 2006/0036259 A1 | 2/2006 | Carl et al. | |
| 2006/0036301 A1 | 2/2006 | Eggers et al. | |
| 2006/0036323 A1 | 2/2006 | Carl et al. | |
| 2006/0036324 A1 | 2/2006 | Sachs et al. | |
| 2006/0047283 A1 | 3/2006 | Evans et al. | |
| 2006/0052782 A1 | 3/2006 | Morgan et al. | |
| 2006/0069447 A1 | 3/2006 | DiSilvestro et al. | |
| 2006/0087325 A1 | 4/2006 | Ariav et al. | |
| 2006/0224088 A1 * | 10/2006 | Roche | 600/587 |
| 2007/0112429 A1 * | 5/2007 | Muhanna et al. | 623/17.15 |
| 2007/0233065 A1 * | 10/2007 | Donofrio et al. | 606/61 |

FOREIGN PATENT DOCUMENTS

| | | |
|---|---|---|
| EP | 0344770 A | 12/1989 |
| EP | 0619101 | 10/1994 |
| EP | 1238630 A | 9/2002 |
| EP | 1285640 | 2/2003 |
| EP | 1442715 | 8/2004 |
| WO | WO9217113 A | 10/1992 |
| WO | WO9733513 A | 9/1997 |
| WO | WO0230338 A | 4/2002 |
| WO | 03/048688 | 6/2003 |
| WO | WO2005007025 A | 1/2005 |
| WO | 2005/062719 | 7/2005 |
| WO | 2005-120167 | 12/2005 |
| WO | WO2006105098 A | 10/2006 |

OTHER PUBLICATIONS

U.S. Appl. No. 11/344,999, filed Feb. 1, 2006 in the name of Donofrio, et al.

* cited by examiner

SENSOR AND METHOD FOR SPINAL MONITORING

FIELD OF THE INVENTION

The present invention is directed to improved instrumentation and methods for monitoring the condition of the spine. More particularly, in one aspect the present invention is directed to a sensor for detecting changes at a spinal level associated with degeneration or injury to the spinal segment.

BACKGROUND OF THE INVENTION

The present invention relates to the sensing changes in tissues associated with a spinal level. The invention may be particularly useful in the assessment of tissue density as it relates to the intradiscal environment. Herniation of disc material or other bulges may lead to patient pain and discomfort. Being able to detect the onset of these conditions may allow early medical intervention to treat the condition, stop its advance or slow the progression. However, it is currently difficult to monitor the condition of the anatomic structures adjacent a spinal segment. Thus, there is a need for a device and system that is able to monitor the spinal segment environment and sense changes that are indicators of potential problems. Early detection of an impending problem provides the surgeon with the ability to identify and treat the affected tissue.

Therefore, there remains a need for improved instrumentation and methods for measuring tissue density and changes in tissue density associated with a spinal segment.

SUMMARY OF THE INVENTION

The present invention provides a method for evaluating a condition of at least a portion of a spinal segment. The method comprises providing a sensor having sensing element and a communication circuit and placing the sensing element in conductive contact with a portion of a spinal segment. In one aspect, the method includes activating the sensor to detect at least one characteristic of the spinal segment and communicating the sensed characteristic of the spinal segment to a user.

In another aspect, the present invention provides a method of treating a patient for a condition in a spinal segment. In one aspect, the method comprises providing a sensor for detecting at least one indicator of spinal segment health and inserting the sensor into the patient adjacent the spinal segment. The method includes sensing a first condition of the tissues associated with the spinal segment, initiating a first treatment course, and sensing a second condition of the tissues associated with the spinal segment after said initiating a first treatment course. In a further aspect, the method includes comparing the sensed first condition to the sensed second condition of the tissues to evaluate the performance of the first treatment course.

In another aspect, the present invention provides a system for monitoring a spinal segment within a patient. In one form, the system comprises a sensor having a sensing portion implantable in the body adjacent to the spinal segment with the sensing portion generating a sensor signal in response to a sensed characteristic of the spinal segment. In one form, the sensor is configured for detecting the condition of the nucleus. In another form, the sensor is configured for detecting the condition of the annulus.

Further aspects, forms, embodiments, objects, features, benefits, and advantages of the present invention shall become apparent from the detailed drawings and descriptions provided herein.

DESCRIPTION OF THE PREFERRED EMBODIMENTS

For the purposes of promoting an understanding of the principles of the present invention, reference will now be made to the embodiments illustrated in the drawings, and specific language will be used to describe the same. It will nevertheless be understood that no limitation of the scope of the invention is intended. Any alterations and further modifications in the described devices, instruments, methods, and any further application of the principles of the invention as described herein are contemplated as would normally occur to one skilled in the art to which the invention relates.

Figure 1:
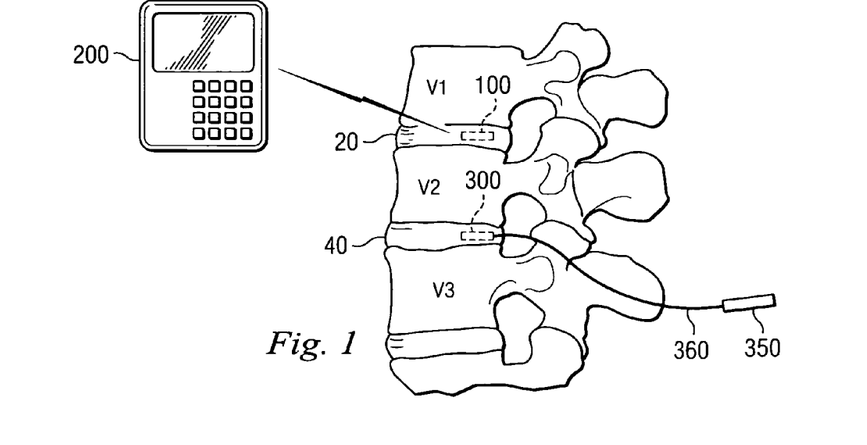
FIG. 1 is a side view of implantable sensors located adjacent the disc spaces in the spinal column according to one aspect of the present invention.

Referring now to FIG. 1, shown therein is an implantable sensor 100 for monitoring changes in tissue density in the disc space area 20 disposed at the spinal level between vertebrae V1 and V2. FIG. 1 shows the implantable sensor unit 100 in wireless communication with an external device 200. In one aspect, the implantable sensor unit 100 is configured to detect and keep track of indicators associated with changes in tissue density. The implantable sensor unit 100 is also configured for wireless communication with the external device 200. Similarly, the external device 200 is configured for wireless communication with the implantable sensor unit 100. In particular, the external device 200 is adapted for retrieving, storing, and displaying, in human intelligible form, the tissue density data detected by the implantable sensor unit 100.

As discussed more fully below, it is fully contemplated that the sensor unit 100 may be disposed at a plurality of locations adjacent the spinal level including, but not limited to, within the disc space or attached to the annulus adjacent to the disc space. Still further, in another aspect the implantable sensor 100 is affixed to bone such that it may monitor adjacent soft tissues, such as nerves and connective tissues. Further, although not illustrated, the implant may be within or integral to an artificial implant, attached to an artificial implant, adjacent to an artificial implant, or any combination of these locations.

Figure 2:
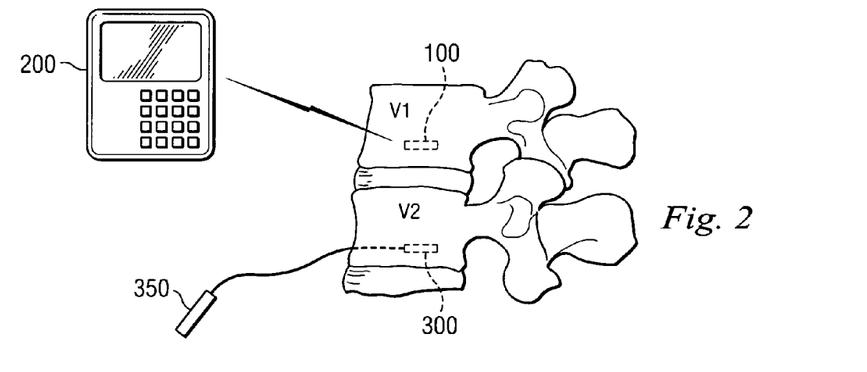
FIG. 2 is a side view of implantable sensors located in the vertebral bodies of the spinal column according to another aspect of the present invention.

FIG. 2 shows the sensor unit 100 adapted for being disposed at least partially within a bone, vertebra V1. In the illustrated embodiment, the outer shell of the sensor unit 100 is substantially similar in shape and size to a bone nail. However, sensor unit 100 may be of any shape or form adapted for placement within a portion of a bone such as vertebra V1. In an alternative embodiment, the sensor unit 100 is substantially shaped like a coin and adapted for placement within a portion of bone.

Figure 3:
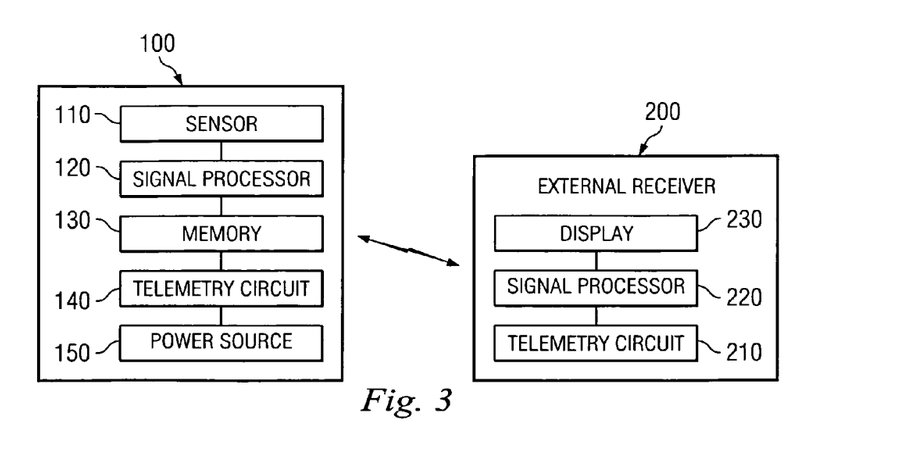
FIG. 3 is a schematic illustration of the wireless implantable sensor of FIG. 1.

Referring to FIG. 3, the implantable sensor 100 includes a sensor 110, a signal processor 120, a memory unit 130, a telemetry circuit 140, and a power source 150. In one embodiment, the sensor 110 is an acoustic transducer responsive to acoustic signals transmitted through human tissue. While the implantable sensor unit 100 is described as having a separate signal processor 120, it is fully contemplated that the function of the signal processor, described below, may be incorporated into either the sensor 110 or the memory 130, eliminating the need for a separate signal processor. Similarly, it is fully contemplated that the functions of the various components of the sensor 100 may be combined into a single component or distributed among a plurality of components. Further, it is fully contemplated that the sensor 100 may include other electronics and components adapted for monitoring indicators of changes in tissue structure including deterioration and/or healing.

The telemetry circuit 140 is adapted for providing power to the acoustic transducer used as sensor 110 and transferring the detected indicators to an external device 200. It is contemplated that the telemetry circuit will provide power to the acoustic transducer via inductive coupling or other known means of passive power supply. It is also contemplated that the external device 200 may be utilized to provide the power to the sensor unit 100 through direct inductive coupling. That is, the sensor unit 100 may be externally powered. Further, this allows the sensor unit 100 to remain in a dormant state whenever an external power supply is not available and then become active when the external power supply is present. In this manner, the sensor unit 100 does not require a dedicated power supply such as a battery. This allows the sensor unit 100 to be much smaller than would otherwise be possible with a dedicated power supply, which in turn allows placement of the sensor in more locations without interfering with body mechanics or functions.

It is contemplated that the sensor is utilized to detect indicators of tissue density over regular intervals such as every day, every week, every month or every 6 months as determined by the treating physician. In this regard, it is contemplated that in one embodiment the patient returns to a doctor's office for each reading. At such time the health care provider would place the external device 200 in the vicinity of the sensor unit 100. Through inductive coupling via the telemetry unit 140 the sensor unit 100 would be powered by the external device 200. The sensor 110 would then take a reading by detecting indicators of tissue density. This reading would then be relayed to the external device 200 via the telemetry circuit 140. The reading may then be analyzed by the health care worker and appropriate medical treatment may be taken. It is also contemplated that in another embodiment the patient obtains these readings without a need to go to the doctor's office. For example, the patient is be provided with the external device 200 that is capable of providing power to the sensor unit 100, obtaining the readings, and then relaying the readings on to the doctor's office. For example, the external device transfers the readings to the doctors office via a phone line or computer network. It is contemplated that a system similar to that of Medtronic's CareLink may be utilized.

The implantable sensor unit 100 may function in a variety of ways. Under one approach the sensor unit 100 uses a type of comparative analysis to determine changes in the tissue properties of the spinal segment. That is, an initial baseline or threshold range of signals will either be determined by the sensor itself or provided to the sensor by the health care provider. Then the sensor 100 will monitor the indicators of tissue properties and when the signals detected are out the threshold range the sensor will store those signals in its memory 130. Then this data is extracted by the health care provider via external device 200. With this data the health care provider then chooses the appropriate treatment plan. For example, the caretaker may choose to have the patient undergo additional examinations such as a CT scan or an x-ray. Either based on the additional examinations or other factors, the caretaker may instead or in addition choose to adjust the threshold range of the sensor.

It is fully contemplated that a treating health care provider may want to change what the sensor considers the normal range of signals overtime. For example, as an artificial implant, such as a artificial disc replacement, is incorporated into the body the signals associated with tissue density near the bone-implant connection point will change until the implant is fully integrated. Further the connective tissue between adjacent vertebral bodies will heal from the trauma of surgery with changes to the connective tissue sensed by the sensor. Once the implant is fully integrated, the normal range of signals from the bone-implant interface and other tissue in the spinal segment may be consistent for a period of months or years. It is contemplated that the sensor 100 be programmable, self-learning, or both to adjust the threshold levels to match the normal range after the healing process has been substantially completed.

Self-learning implies that the sensor 100 is able to determine the proper range of signals by monitoring the signals over a period of time and then via algorithms in its signal processing unit to decide on the range of signals indicative of normal tissue characteristics adjacent the spinal segment. In this regard, it is fully contemplated that the health care provider may be able to override the determinations made by the sensor 100 by programming in the thresholds or, on the other hand, the caretaker may reset the sensor's determinations and simply have the sensor recalculate the proper range based on current signals detected. Thus, as described above when an implant becomes fully integrated the caretaker may decided to reset the self-learning sensor so that the ranges are based on the signals associated with the fully integrated implant.

In regards to setting the ranges, it is contemplated that in one embodiment the patient is instructed through a series of movements such as sitting down, standing up, walking, climbing stairs, or cycling with the sensor 100 detecting the associated indicators of tissue characteristics such as for example, but without limitation to other sensed characteristics either alone or in combination with density, elasticity, size, inflammation, temperature, Ph, blood flow, pressure, electromyography (EMG) signals, and nutrient flow in the spinal segment of interest. Based on the sensed signals, the sensor threshold ranges are set for operation. For example, the acoustic signals produced by these and other movements are detected within a bone or other tissue being monitored. Thus, instructing the patient through many of the normal motions and movements of everyday life provides a good variety of signals that may be used to base the normal signal range upon. Over time, the patient may again be put through a similar series of movements to reset or recalibrate the sensor 100 as seen fit by the caretaker. Further, changes in detected characteristics during the series of movements may be used to diagnosis a patient's condition based on comparing the sensed properties in one activity to the sensed properties in a different activity or position.

Under another approach, the sensor 100 may function by monitoring for signals associated with the onset of annulus tears, annulus herniation, bulging discs or other changes in tissue density, tension, or shape. For example, there are certain acoustic sounds and vibrations associated with degenerating conditions in the spinal segment, including the intradiscal environment. In this embodiment, the sensor 100 is configured to detect and recognize these acoustic signals. For example, the sensor 100 utilizes various filters, amplifiers, and algorithms to remove background noise and focus on the detection of the signals indicative of degenerating conditions in the intradiscal structures or other changes in tissue density. Though in the currently described embodiment the sensor 100 is an acoustic sensor, it is also contemplated, and described more fully in U.S. patent application Ser. No. 11/344,667 entitled IMPLANTABLE SENSOR, by Donofrio, et al., filed Feb. 1, 2006 incorporated herein by reference in its entirety, that the sensor 100 may utilize a variety of sensing features, including impedance, to detect changes in tissue density.

In the case of an acoustic sensor 110 as in one embodiment, the acoustic transducer is configured for detecting sounds and acoustic waves indicative of tissue density. Under one approach if the detected signal exceeds the normal range of signals as determined by the signal processor 120, then the signal will be stored in the memory 130. In this regard, the signal processor 120 is configured to determine the parameters or threshold levels of signal ranges for detection by the sensor 100. The signal processor 120 sets parameters such as the amplitude, frequency range, or decibel level required before a signal is considered an indication of a change in tissue density. The range and parameter settings may be configured so as to increase the accurate detection of changes in tissue density.

The memory 130 is configured to store data it receives from the signal processor 120 that is either outside the normal signal range or within the range of signals being detected. It is fully contemplated that the memory 130 may utilize known compression algorithms and functions to save on memory and size requirements. In this regard, it is also contemplated that the memory 130 may store additional data with respect to each signal such as a timestamp, the specific characteristics of the signal, or any other relevant data. In this respect, the signal processor 120 and memory 130 are configured to keep the various types of data the orthopedic surgeon or treating physician would like to have to monitor tissue density.

The implantable sensor 100 also includes a telemetry circuit 140. The telemetry circuit 140 is connected to the memory 130 and is adapted for sending the data stored in the memory outside of the patient's body to an external device 200. In particular, the telemetry circuit 140 is adapted for communicating wirelessly with the telemetry circuit 210 of the external device 200. There are several types of wireless telemetry circuits that may be employed for communication between the implantable sensor 100 and the external device 200. For example, RFID, inductive telemetry, acoustic energy, near infrared energy, "Bluetooth," and computer networks are all possible means of wireless communication. In the present embodiment, the telemetry circuits 140, 210 are adapted for RFID communication such that the telemetry circuit 140 is a passive RFID tag. In one aspect, the sensor is also programmed with identification information concerning the type of procedure performed, the date of the procedure and the identification of the medical devices implanted. Using a passive RFID tag helps limit the power requirements of the telemetry circuit 140 and, therefore, the implantable sensor 100 yet still allows wireless communication to the external device 200.

Supplying the power requirements of the implantable sensor 100 is a power source 150. In the current embodiment, the power source 150 is a battery. In this manner the sensor may be internally powered. The battery power source 150 may be a lithium iodine battery similar to those used for other medical implant devices such as pacemakers. However, the battery power source 150 may be any type of battery suitable for implantation. The power source 150 is connected to one or more of the transducer 110, the signal processor 120, the memory 130, or the telemetry unit 140. The battery 150 is connected to these components so as to allow continuous monitoring of indicators of tissue density. It is fully contemplated that the battery 150 may be rechargeable. It is also contemplated that the battery 150 may be recharged by an external device so as to avoid the necessity of a surgical procedure to recharge the battery. For example, in one embodiment the battery 150 is rechargeable via inductive coupling.

In one embodiment, the sensor 100 is passive. However, it is fully contemplated in an alternative embodiment that the sensor 100 be active. Where the sensor 100 is active, the transducer 110 uses a pulse-echo approach to detect various aspects of tissue density, including without limitation to other features, nutrient channel porosity, nutrient channel flow, nutrient channel calcification, annulus elasticity and tissue inflammation. For example, utilization of ultrasonic waves in a pulse-echo manner to determine tissue density is fully contemplated. In that case, the transducer 110 would utilize power from the power source 150 to generate the pulse signal. In the current embodiment, however, the transducer 110 may use the power source 150 to facilitate the sending of signals to the signal processor 120. The signal processor 120, in turn, may use the power source 150 to accomplish its filtering and processing and then send a signal to the memory 130. The memory 130 will then use the power source 150 to store the signal and tissue density data.

In other embodiments the power source 150 may also be connected to the telemetry circuit 140 to provide power to facilitate communication with the external device 200. However, in the present embodiment the telemetry circuit 140 does not require power from the power source 150 because it communicates with the external receiver 200 utilizing a passive RFID tag type or other inductive coupling means of communication. Further, the power source 150 may be connected to other electronic components not found in the current embodiment. It is fully contemplated that the power source 150 may include a plurality of batteries or other types of power sources. Finally, it is also contemplated that the implantable sensor 100 may be self-powered, not requiring a separate power supply. For example, a piezoelectric transducer may be utilized as the acoustic transducer 110 such that signals detected by the transducer also provide power to the sensor 100. The piezoelectric transducer could detect the signal and converts it into an electrical signal that is passively filtered and stored only if it satisfies the signal thresholds. Then, as in the current embodiment, the sensor 100 may utilize a passive RFID tag or other passive telemetry unit to communicate the tissue density data with an external device. Thus, allowing the sensor 100 to function without a dedicated or continuously draining power source. Similarly, the sensor 100 may utilize a piezoelectric or electromagnetic power source that is not used as the acoustic transducer 110. For example, such power sources could utilize patient motion to maintain a power supply.

Referring now to FIGS. 1 and 2, shown therein is an alternative embodiment of a sensor for monitoring the spinal environment in accordance with another aspect of the present invention. The sensor system is substantially similar to the other sensors described in accordance with the present invention. However, the sensor system includes a transducer lead 300 for insertion into a disc space or bone (FIG. 2) and a separate main housing 350. In one aspect, the main housing 350 contains the remaining components of the sensor system such as a signal processor, memory unit, telemetry unit, power supply, and any other component. As illustrated, the main housing 350 is adapted to be positioned away from the transducer leads 300. Main housing 350 is located outside of the exterior of the spinal column. In a further aspect, main housing 350 is attached to the bone 10 or positioned within surrounding soft tissue. Positioning the main housing 350 away from the transducer 300 allows the transducer, which may be miniaturized, to be placed in a desired location without requiring the additional space to house the remaining components of the sensor system. In one embodiment, the main housing 350 is shaped as a substantially cylindrical housing so as to facilitate implantation via a catheter.

In one aspect, transducer 300 is substantially cylindrical such that it can be delivered to the implantation site via a needle or catheter. In this respect, the transducer 300 may communicate with the components in the main housing 350 via a dedicated wire or lead 360, as shown. In a further embodiment, the transducer 300 communicates with the components in the main housing 350 wirelessly. For example, the transducer 300 utilizes an RF transponder or other means of wireless communication to transfer information to the main housing 350.

Though the main housing 350 is shown as being disposed inside the body and near the spine, in another application the main housing is disposed anywhere within communication range of the transducer 300, including outside the body. Thus, the main housing 350 is preferably located where it will not interfere with the function of the spine nor interfere with any other body functions. Where the transducer 300 communicates with the components of the main housing 350 via the wire lead 360, the location of the main housing is limited by potential interference of both the wire and the main housing. Where the transducer 300 communicates with the components in the main housing 350 wirelessly, the position of the main housing 350 will be a function of the limits on the distance for wireless communication as well as any potential body function interference the main housing may cause. With sufficient wireless communication, the main housing 350 is positioned outside the patient's body. Preferably, when disposed outside of the body the main housing 350 will be positioned in a location anatomically close to the transducer 300. Placing the main housing 350 as close to the location of the transducer 300 as possible helps to facilitate wireless communication. It is not necessary to place the main housing 350 near the transducer 300 if communication can be achieved from greater distances.

The sensors 100 and 300 may take a variety of forms, shapes and sizes without deviating from the present invention. For the purpose of illustration but without limitation to alternative designs, in the illustrated embodiments the sensors are of the type to sense acoustic energy, RF energy, light energy, chemicals, PH, temperature, biologic compounds and/or electrical conductance such as impedance. Further the sensors incorporate more than one type of sensor to permit sensing of multiple tissue characteristics with a single sensor or network of associated sensors. In a further aspect, a first tissue characteristic and a second tissue characteristic are sensed. The first and second characteristics are compared, and the comparison is utilized as an indicator of tissue condition. In a still further aspect, more than two tissue characteristics are compared to generate a tissue condition. Various attributes of implantable sensors are more fully described in U.S. patent application Ser. No. 11/344,459 entitled METHODS FOR DETECTING OSTEOLYTIC CONDITIONS IN THE BODY, by Nycz, et al. filed Jan. 31, 2006 incorporated herein by reference in its entirety. The sensor has a shape adapted to the planned implantation technique or location in the body. For example, but without limitation to alternative shapes, the sensor may have the shape of a sphere, cylinder, rectangular, elongated thin film, circular thin film, or may include a housing of one of these shapes with leads extending to the tissue of interest shape. In one aspect, the spherical sensor would have a diameter less than 2 cm, more preferably less than 1 cm and still more desirable but not required, the diameter would be less than 2 mm. In a similar manner, it is contemplated that cylindrically shaped sensors will be sized to pass through insertion devices such as catheters and needles suitable for minimally invasive insertion. For example, the cylindrical sensor body may have a diameter less than 2 cm, more preferably less than 1 cm and still more desirable but not required, the diameter would be less than 2 mm. The length of the cylindrical implants may vary depending on the expected application with typical devices ranging from 15 cm to less than 1 cm in length. With continued improvements in micro-scale and nano-scale technology it is contemplated that still smaller diameter sensors may be used alone or in combination with a plurality of very small sensors sensing tissue at different locations. In one aspect, the thin film embodiments have a perimeter of a desired shape and size for the expected application in the body or insertion technique and have a thickness less than 5 mm and more desirably a thickness less than 2 mm.

The sensors 100 and 300 include processor and memory components to process the sensed signals and store the information for later retrieval or transmission. In one form, each sensor is formed for a particular application with a static program having features specific for the intended medical application. In another form, the sensor is of a universal type with a programmable memory and processor. With the universal sensor embodiment, it is contemplated that the sensor will be supplied in bulk. The sensor will be programmed to operate to sense the desired tissue characteristics of interest, report sensed signals outside of the established threshold values and report the information according to the programmed instruction set. In one aspect, the operational program of the universal sensor is burned-in at a production facility and packaged alone or with an associated implant. In this manner, the program may not be altered by the user. In a different form, all or a portion of the operational program is installed at a production facility into a programmable sensor and the user may add to, change, erase and/or reprogram the sensor after delivery to the user to suit their needs. It is contemplated that the programmable sensor is updated by the user prior to implantation in a patient, during the implantation procedure or at any time after implantation. In this form, all or a portion of the sensor includes an erasable programmable memory (EPROM) of flash memory. Still further, the sensor may output data by wired or wireless telemetry in any manner. Examples of various formats are provide in U.S. patent application Ser. No. 11/344,667 entitled IMPLANTABLE SENSOR by Donofrio, et al. filed Feb. 1, 2006, incorporated herein by reference in its entirety.

The sensors 100 and 300 of the present invention may be implanted into the body in a variety of surgical procedures. It is contemplated that the approach to the patient should involved the least damage to the patient's tissue as possible. In one aspect, implantation of the sensor is conducted via an open surgical procedure, particularly when implanted in conjunction with other load bearing implants. For example, during the exposure necessary for an interbody fusion between adjacent vertebrae V1 and V2, a sensor is placed in the native bone, the fusion mass or the adjacent soft tissue. Similarly, a sensor may be placed in conjunction with the implantation of motion preserving prostheses such as artificial discs, nucleus replacement, facet replacements and dynamic stabilization devices. However, in another aspect, it is expected that implantation of the sensor will be through a minimally invasive procedure adapted to minimize trauma to the patient. For example, in one embodiment a guide member such as a needle or guidewire is positioned through the skin to a position adjacent a spinal segment. A tubular member, such as a needle or other cannula, having an internal diameter larger than the external diameter of the guide member is positioned over the guide member. The guide member is withdrawn leaving a passage to the implantation site adjacent the spinal segment. A sensor, such as a cylindrical or spherical shaped sensor, may then be passed through the tubular member to the implantation site. Additional features of the sensor, the implantation instruments and surgical techniques are disclosed in U.S. patent application Ser. No. 11/344,999 entitled IMPLANTABLE PEDOMETER by Donofrio et al. filed Feb. 1, 2006 incorporated herein by reference in its entirety.

In one aspect, the sensor will be placed in tissue that will have sufficient tissue strength to maintain its position in the body. For example, in one embodiment the sensor includes an exterior surface feature for engaging the bone of a vertebral body. In still a further embodiment the external surface is roughened or bristled to engage the soft tissue adjacent to the a spinal segment. In still a further embodiment, the sensor is placed subcutaneously spaced from the spinal column with sensing means to sense tissue characteristics of the spinal column. In other implantation procedures, the sensor unit 100 is press-fit into an opening formed in a bone. It is contemplated that after the sensor unit 100 has been press-fit into the prepared opening that it may then be sealed into the bone. The sensor unit 100 may be sealed into the bone using a variety of techniques. These sealing techniques may include, but are not limited to, fibrin glue, PMMA, collagen, hydroxyapatite, biphasic calcium, resorbable polymers or other materials suitable for implantation. Additionally or alternatively, in another embodiment the sensor unit 100 is sealed into the bone by a later implanted implant, or any combination of these techniques. For example, the sensor unit 100 is sealed in by any of the above mentioned materials in combination with an additional implant to provide enhanced fixation. In this manner, the sensor unit 100 is implanted either prior to the implantation of an implant or as a stand alone unit—where no implant is to follow.

Still further, in an alternative embodiment the sensor includes sensor 300, lead 360 and a main body 350 such as the sensor shown in FIGS. 1 and 2. In one aspect, the sensors 300 are implanted at least partially within the disc space to sense the intradiscal environment. In an alternative embodiment, the sensors 300 are positioned in contact with or adjacent to the annulus between adjacent vertebral to sense signals indicative of the annulus or disc environment. In still a further embodiment, the sensors 300 are placed approximate the exiting nerve roots to detect signals indicative of nerve condition and health. The leads are placed in any position suitable to detect the environmental condition of the spinal segment. In each of these positions, the main body 350 of the sensor is positioned away from the sensing leads to limit interference with normal patient function and movement or to provide easier communication and powering by external devices. While it is contemplated that the main body 350 will be implanted, in one embodiment the main body 350 is positioned outside the patient with wired or wireless communication occurring between the sensing leads and the main body.

As shown in FIGS. 1-4, the external device 200 receives the tissue density data from the implantable sensor 100 or main housing 350 via communication between the telemetry circuit 140 of the sensor and the telemetry unit 210 of the external device. Then a signal processor 220 converts or demodulates the data. The converted data is output to a display 230 where it is displayed in human intelligible form. The conversion and processing of the data may be tailored to the specific liking of the health care provider. For example, the display of data may simply be a number representing the number of signals recorded by the memory 130 indicating the number of signals outside the normal range that were detected. Similarly, the display of data may be a bar graph having a height or length representing the number of signals detected. Further, the display may show a detailed chart of specific information for each signal detected outside of the threshold range. These various display examples are for illustration purposes only and in no way limit the plurality of ways in which the tissue density data may be displayed in accordance with the present invention.

Figure 4:
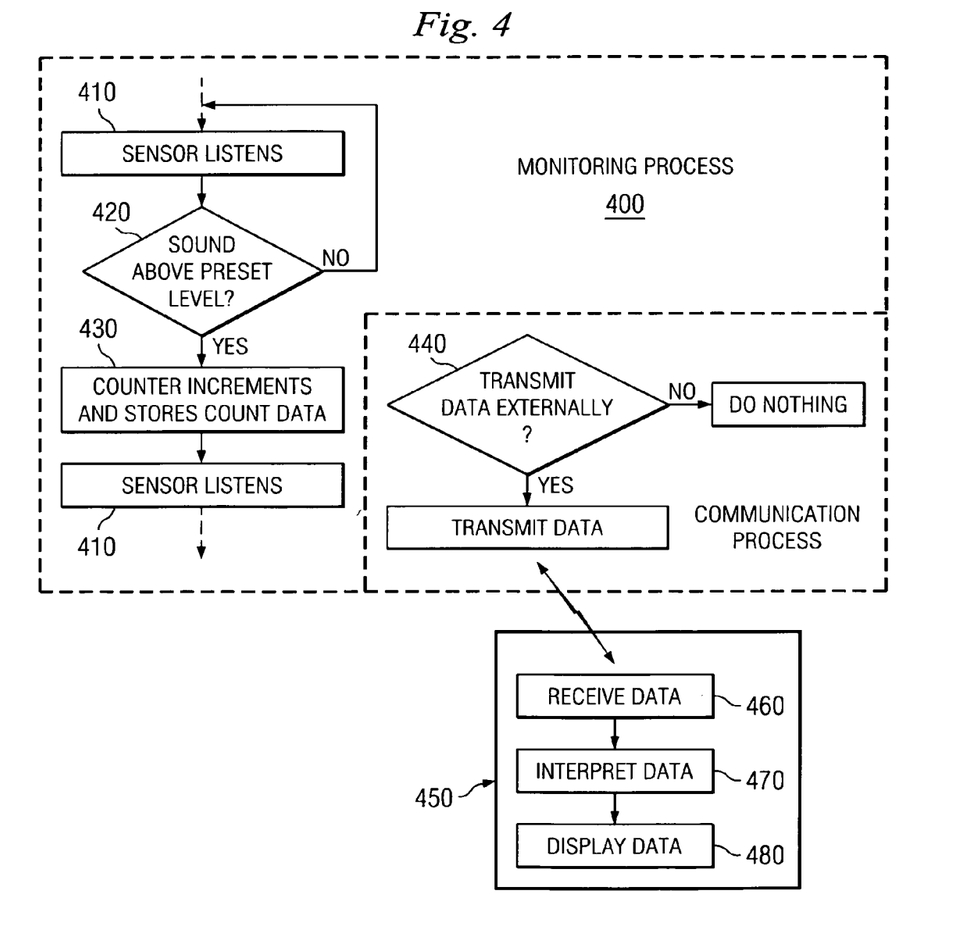
FIG. 4 is a flow chart illustrating use of the implantable sensor and external receiver of FIG. 1.

FIG. 4 illustrates one embodiment of a flow chart for tissue density data detection, processing, and output employing the current embodiment of the invention. The internal monitoring process occurring within the sensor 100 constitutes a continuous loop of monitoring and storing the tissue density data. In step 410, the acoustic transducer 110 listens for signals indicative of tissue density. Upon detecting a signal the signal processor 120 determines in step 420 if the signal meets the preset parameters. If the signal does not meet the thresholds, then the signal processor 120 does nothing and returns to listening 410. If the signal does meet the parameters, then the signal processor 120 passes along a signal to the memory 130. The memory 130 stores the tissue density data accordingly at step 430. The internal process returns to step 410 as the acoustic transducer 110 listens for the next tissue density signal.

Also within the sensor 100, a communication process is underway. In step 440, the telemetry unit 140 awaits communication from the external device 200 requesting transmission of the tissue density data. If the telemetry unit 140 receives such a request, then at step 450 the telemetry unit 140 transmits the tissue density data to the telemetry unit 210 of the external receiver 200. At step 460, the receiver receives the data and the signal processor 220 converts or demodulates the transferred data at step 470. The display 230 displays the demodulated data in a human intelligible form at step 480. At this point the surgeon or other health care provider can review the tissue density data and take the appropriate medical action as they see fit.

Though not illustrated, it is also contemplated that one embodiment the external device 200 resets the tissue density data stored within the sensor 100. For example, the external receiver 200 is configured to reset or clear the memory 130 upon extraction of the tissue density data. The external device 200 may clear the memory 130 of the sensor 100 by utilizing communication between the telemetry circuits 140, 210. However, it is not necessary for the external device 200 to clear the data of the sensor 100. For example, a treating physician may wish to keep a running count of signals detected outside the normal range in the memory 130 rather than resetting the sensor 100 after each data extraction.

Described below are numerous components of the external receiver in accordance with the present invention. These components illustrate the various types of electronic and non-electronic components that may be utilized by the external receiver. These descriptions are exemplary of the type of components that may be employed by the external receiver, but in no way are these illustrations intended to limit the types or combinations of electronic and non-electronic components that may be utilized in accordance with the present invention.

The external receiver may include components such as a telemetry unit, a signal processor, a calibration unit, memory, an indicator, and a networking interface. The telemetry unit is adapted for communication with the implantable sensor in accordance with the present invention. Thus, the telemetry unit is configured to extract tissue density data from the sensor. The telemetry unit may obtain data from the sensor through a variety of wireless communication methods such as inductive coupling, capacitive coupling, radio frequency, personal computer networking, Bluetooth, or other wireless means. Though the preferred method of communication is wireless, it is also contemplated that the external receiver may be in selective wired communication with the implantable sensor.

Once the data is obtained by the external receiver using the telemetry unit, the data is processed by the signal processor. The degree and type of data processing is dependent on both the data obtained from the implantable sensor and the desires of the treating doctor. The data processing performed by the signal processor may range from simple conversion of tissue density data into a human sensible form to complex analysis of the usage data via spectral analysis. Further, the data processing performed by the signal processor may only be a first step of processing. The processed data of the external receiver may be output to a more powerful or specialized signal processing unit where additional processing takes place. This additional signal processing unit may be located either within the external receiver itself or in a separate external device such as a personal computer.

The signal processor is adapted for converting the data into a form that may be utilized by an indicator. The indicator may be any type of device or interface that can output the data in human intelligible form. For example, the indicator may be a visual display, speaker, or any other indicator or output means. It is contemplated that the indicator may be composed of a plurality of output mechanisms instead of a single device.

The external receiver includes a calibration circuit in one embodiment. The calibration circuit is adapted for configuring a configurable signal processor of an implantable sensor. The external receiver may set, restore, or change such aspects of the configurable signal processor as the predetermined criteria for keeping sound recordings, the type of tissue density data to be kept, the preset thresholds for signals indicative of normal tissue density, or any other setting related to the performance of the configurable signal processor. It is fully contemplated the calibration circuit may utilize the telemetry circuits of the sensor and external receiver to communicate with the configurable signal processing unit. However, it is also fully contemplated that the calibration circuit and the configurable signal processing unit may have a separate dedicated means of communication.

In one embodiment, the external receiver includes a memory unit. The memory unit may be adapted for multiple uses. First, the memory unit may be adapted for permanent storage of tissue density data obtained from the implantable sensor. Thus, the memory unit may store data obtained at various times from the implantable sensor so the data may later be reviewed, compared, or analyzed. Second, the memory unit may be adapted for temporary storage of tissue density data obtained from the implantable sensor. In this case, the memory unit will store the data until it is either discarded or transferred for permanent storage. For example, the data may be transferred from the memory unit of the external receiver via a networking interface to a network or computer for permanent storage.

When present, the networking interface provides a means for the external receiver to communicate with other external devices. The type of network utilized may include such communication means as telephone networks, computer networks, or any other means of communicating data electronically. The networking interface of the external receiver could obviate the need for the patient to even go into the doctor's office for obtaining implant usage data. For example, the patient could utilize the external receiver to obtain the usage data from the implantable sensor on a scheduled basis (e.g. daily, weekly, monthly, etc.). Then, utilizing the networking interface the patient could send this data to the treating doctor. In one aspect, the networking interface is configured to directly access a communication network such as a telephone or computer network for transferring the data. It is fully contemplated that the computer network be accessible by a treating physician for reviewing implant usage data of the patient without requiring the patient to make an actual visit to the doctor's office. The networking interface may be similar to the CareLink system from Medtronic, Inc.

Further, it is also contemplated that any communication between the external receiver and the computer network may be encrypted or otherwise secured so as protect the patient's privacy. It is also contemplated that the networking interface may be configured for communication with a separate device that is adapted for accessing the communication network. For example, the networking interface may be a USB connection. In one embodiment, the external receiver is connected to a personal computer via the USB connection and the personal computer is be utilized to connect to the communication network, such as the internet, for transferring the data to a designated place where the treating doctor may receive it.

The disclosed sensors for detecting indicators of changes in the spinal segment environment are utilized in numerous applications. For example, but without limitation to other uses, in one embodiment the detected changes are used to predict the onset of herniation of the disc, disc bulges, annulus tears, degeneration of the disc nucleus, inflammation, pain localization, myelin sheath changes, presence of abnormal chemical or biologic agents, therapeutic agent concentrations, spatial relationship of spinal components, pressure, tension, relative motion between spinal components, bone growth, nutrient channel function, facet function, adhesion growth and location, instantaneous axis of rotation, implant usage, implant degradation, and presence and amount of particles. Further, in another aspect the sensors are placed at a first spinal level to provide data on the localized conditions and similar sensors are placed at other spinal levels to provide similar sensed data for comparative analysis for diagnosis and treatment.

In one aspect, sensors of the present invention may be used in diagnosis of patients presenting with spinal pain or degeneration. At times, it is difficult for the healthcare provider to identify with certainty the precise cause of the back pain being experienced by the patient. Even after imaging the spine, the area causing the pain may not be readily identifiable. In this aspect, one or more sensors in accordance with the present invention is placed adjacent one or more spinal segments prior to provide sensed data to the health care provider. For example, but without limitation, in the case of radiculitis where the pain is diffuse, the sensors are programmed to seek characteristics of inflamed nerves adjacent each spinal segment. For example, sensors at multiple levels may gather data on the size and geometry of the exiting nerve roots. Based on comparative analysis, the surgeon may be able to more accurately determine the nerve root causing the pain. Further, in an additional embodiment the sensors also include chemical or biologic sensors to detect the presence of inflammatory agents adjacent the nerves. This would be an indicator of nerve distress and potential patient pain. Still further, in one embodiment a sensor is configured to detect electromyography (EMG) signals associated with muscle stimulation. Other useful sensors that are used alone or in combination with the foregoing sensors include temperature or PH to detect changes in the body indicative of a localized response to pain transmission. With this information, the care giver may determine the course of non-invasive treatment or surgical options. For example, in one method a first treatment course of a first pharmaceutical compound or compounds at a first dosage is prescribed for a first period. The sensors evaluate the indicators of nerve inflammation and provide the sensed data to the care giver. Based on the sensed data, the treatment continues if there is sensed a positive change in the patient. However, if the sensors detect little change or a worsening condition, the first pharmaceutical compound or compounds is changed to a second treatment course of a second dosage, or alternatively a second pharmaceutical compound or compound is prescribed at a third dosage. The process of treating with pharmaceuticals and sensing changes in the patient continues indefinitely as desired by the caregiver and patient. As explained further below, in another aspect this process is automated by having the sensor data transmitted to an indwelling supply of a treatment agent that can be released as sensed data crosses the programmed thresholds. Moreover, in one aspect the sensor notifies the patient of conditions needing urgent attention as soon as possible and of degenerating conditions needing attention in a matter of days, weeks or months.

In another application, sensors according to the present invention are positioned to monitor the intradiscal space. For example, the nutrient system supplying the nucleus may be evaluated to determine whether non-invasive or minimally invasive treatments may be effective for the patient. In one aspect, the sensor is configured to evaluate the openings in the endplates of the vertebrae adjacent the disc space. These openings allow nutrients to flow into the disc space and nourish the disc nucleus. In one aspect, the sensors are be programmed to detect the size, spacing and distribution of the nutrient openings to provide an assessment of the expected flow of nutrients. Further or alternatively, in another aspect the sensors detect the presence and concentration of one or more nutrients to evaluate the health of the nutrient flow. If the health of the nutrient flow system is sufficient, the health care provider may prescribe a first treatment course of patient rest, external mechanical unloading of the segment or minimally invasive internal mechanical unloading of the segment. In these conditions the nucleus may heal to substantially its normal condition. In one treatment method, as part of the first treatment course the care provider also prescribes pharmaceutical agents to increase the nutrients reaching the nucleus. For example, but not as an exclusive listing, pharmaceutical agents such as pain killers, steroids, anti-inflammatory drugs, growth hormones or factors may be taken orally, injected, delivered intravenously, delivered transdermally, metered with a pump or placed on a microchip assay. Either indwelling or instrument placed sensors are used to monitor the tissues adjacent the spinal segment being treated. If the sensed changes are above a first threshold value indicating a worsening condition, the patient is switched to a second course of treatment compounds and/or surgical intervention. In the alternative, the sensed data may indicate that conservative care is unwarranted and urgent surgery to remove all or a portion of the nucleus, or an operation to open existing nutrient channels in the endplates or create new nutrient channels in the endplates is the best course of care. Thus, the sensor system according to the present invention detects the disc nucleus system health and provides data to select between non-invasive, minimally invasive and invasive procedures to treat the sensed disc space condition.

In still a further treatment option, sensors according to the present invention are left in a patient indefinitely to provide periodic information on the spinal segment conditions. Comparative analysis of the periodic readings provides the care giver with a picture of the current health of the spinal segment and the ongoing patient health trend. With this information, the care giver advises the patient of the appropriate treatment option along the continuum of care available to health care providers treating a patient suffering from back problems. For example, but without limitations to alternative treatments, in one aspect the care provider advises the patient in a first treatment course to make life style changes; including diet, nutritional supplements, rest and exercise. Based on sensed data, a second treatment course is initiated that includes, for example, a treatment compound regime; physical therapy; an increase or alteration of a current pharmaceutical regime; seek non-invasive intervention including external mechanical unloading, therapeutic agent pumps, transdermal delivery devices; seek minimally invasive intervention often without joint capsule invasion; or seek invasive treatments to the spinal segment often with joint capsule invasion. Examples of minimally invasive intervention include facet spacers, spinous process spacers, tethering, and dynamic stabilization. Examples of invasive intervention include nucleus replacement, interbody fusion, artificial disc placement, posterior fixation, anterior fixation and lateral fixation. Each of the above can be considered a first treatment course with each successive treatment, including cessation of the first treatment, being the second treatment course, the third treatment course, etc. until patient relief is obtained.

The sensors of the present invention are designed to be used intraoperatively. For example, sensors are placed on or near the annulus of the affected spinal segment disc space and/or the facet joint connective fibers defining the facet joint annulus. The sensor or sensors detect the condition of the annulus during disc space distraction and interbody spacer placement. In one embodiment, the sensor provides the surgeon with an indication of whether the proper annulus tension has been reached and a warning when the annulus tension exceeds the desired amount such that permanent damage is imminent with further distraction. In one aspect, an additional sensor is placed on or near an adjacent spinal level annulus. In this aspect, the tension in the affected spinal segment annulus is compared to the adjacent level annulus, such that the surgeon may tension the affected level annulus to approximate the tension sensed in the adjacent spinal level annulus. In one aspect, evaluation of the annulus includes sensing the characteristics of sharpie fibers within the annulus walls. The sharpie fibers are a part of the annulus adhered to the bone and may experience thinning or bulging in degenerative conditions and during excessive intraoperative distractions.

A still further use of spinal segment sensors according to the present invention is to determine the instantaneous axis of rotation (IAR) of one or more spinal segments. In this application, the sensor is configured and programmed to sense the IAR of a spinal segment and transmit the sensed data to a health care provider. A series of measurements is taken indicating the relative position of the endplates and/or vertebral bodies in various patient positions. The system can then determine the IAR of the one or more spinal segments from the sensed data. Either manually or via computer, the data is used to determine the ideal position for the location of an implant within the disc space to reproduce the ideal IAR. The placement of an implant to maintain or restore the natural IAR can be important to prevent the IAR of adjacent spinal levels from changing as a result of the implant placement or the improperly placed implant may wear more quickly or dislodge as a result of being off center from the natural IAR and the resultant peak forces.

In another aspect of the present invention, sensors remain in place or are positioned during a surgical operation on an affected spinal segment. The sensor(s) provides data to the care giver concerning the healing of the affected spinal segment. For example, the sensor is programmed to detect the presence and location of adhesions adjacent the surgical site. This may assist the care giver in rehabilitation treatment and/or the need for surgical release of the adhesions. Further, the sensors monitor the patient and implant range of motion early in the recovery process to ensure the best possible outcome. Experience has shown that waiting too long after surgery to recover the full range of motion may inhibit the patient from ever obtaining the full range of motion of the normal spinal segment. Moreover, in an additional aspect the sensor monitors patient compliance with rehabilitation programs such as stretching, exercise and rest. Historical range of motion data from the sensors can also be used to evaluate the ability of the patient to work in a given occupation and/or qualify for workers compensation benefits. Still further, the sensed information detects patient behavior detrimental to the healing process such as too much strenuous activity too early after surgery. These conditions can be addressed with the patient by the care giver. For example, a first course of rehabilitation care may be initiated following an initial treatment. Based on sensed data indicating the healing and/or health of the spinal segment, a second course of rehabilitation care may be initiated. If the sensors are left in place indefinitely, they can be periodically accessed to provide historic data on implant usage, particle debris presence and concentrations such as silicone or carbon fiber particles.

In yet another aspect, a sensor according to the present invention is positioned to monitor the intradiscal space to evaluate healing and general health characteristics. For example, in this application the sensor periodically checks the endplate nutritional channels to evaluate size and distribution to assess potential calcification in progress. Further, the sensor detects the flow, presence, and/or concentration of nutrients in the fluid of intradiscal space to provide an approximation of the disc space health. The sensor may also detect the properties of the nucleus, such as height, density, water content, and mineral content to evaluate the health of the nucleus. In still a further embodiment, either in combination with the other sensor features or separately, a sensor monitors the intradiscal space for temperature, PH and the presence of inflammatory response agents such as cytokines. The sensor, or an external device, records readings over a period of time to indicate to the patient or care giver the presence of conditions needing immediate medical attention or degenerative conditions needing attention at some point in the next few days, weeks or months.

Figure 5:
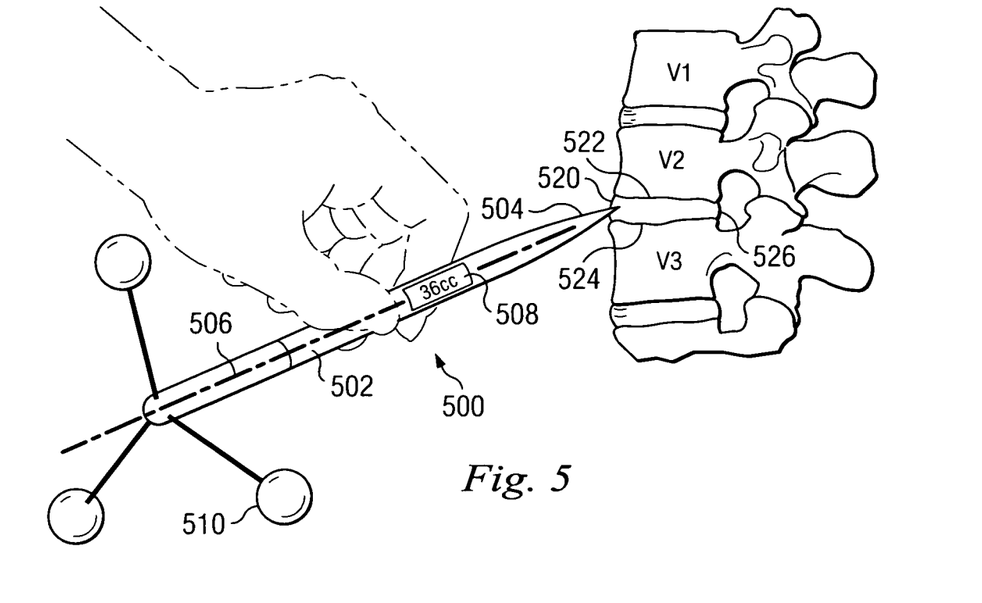
FIG. 5 is a side view of a hand held sensor according to another aspect of the present invention.
Figure 6:
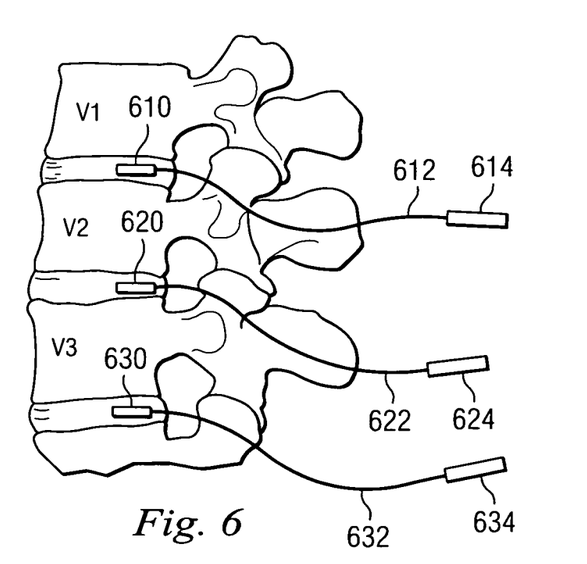
FIG. 6 is a side view of a series of sensors according to another aspect of the present invention.

Referring now to FIGS. 5 and 6, there is shown instrumentation for use in or in conjunction with surgical procedures. Each figures shows a portion of the vertebral column with vertebral bodies V1, V2 and V3 separated by intervening disc spaces. In FIG. 5, a sensing instrument 500 is shown. Instrument 500 has a main body 502, a proximal end 504, and a distal end 506. The main body 102 includes a gripping surface 508 for grasping by the user or engagement with a further instrument. The proximal end 504 is adapted for placement adjacent the annulus surface 520 of the disc space being assessed when the electronic instrumentation 500 is in use. Thus, the distal end 506 is disposed distally to the tissue being assessed when the electronic instrumentation 500 is in use. The electronic instrumentation 500 of FIG. 5 also includes a display 508 and a fiducial marker assembly 510. The fiducial marker assembly 510 is joined to distal end 106. A longitudinal axis extends along at least a portion of the main body 502.

The main body 502 is adapted for housing the various electronic components of the electronic instrumentation 500. In FIG. 5, the main body 502 is shown as being substantially cylindrical and elongated. This is merely for illustrative purposes. It is fully contemplated that the main body 502 may take any shape capable of holding the components of the electronic instrumentation 500, including non-cylindrical and non-elongated designs. However, it is preferred that the main body 502 be of appropriate shape and size to be portable and handheld. For example, but without limitation, in further embodiments the main body is shaped similar to an injector gun, laser pointer, or pen. Still further, in another embodiment the main body 502 is narrow like a catheter or needle and is manipulated remotely for minimally invasive surgery.

The tip 504 is shown extending through annulus 520 between superior vertebral body V2 and inferior vertebral body V3. The sensor associated with instrument 500 includes the same sensing capabilities discussed above with respect to the implantable sensors 100 and 300 and may be used in the same manner on a handheld or percutaneous basis. Once positioned in the disc space, the sensor evaluates the vertebral endplates 522 and 524. For example, it determines the total volume of the space between the endplates and annulus to thereby calculate the proper sizing of a spacing implant to be inserted into the disc space and/or the amount of filling material to be inserted into the disc space to promote fusion between V1 and V2. Further, as described more fully above, the sensor instrument 500 is used to evaluate the nutrient channels extending through endplates 522 and 524. In a further aspect, the sensor detects the extent of herniation or bulging of the posterior portion 526 of the annulus. It is often necessary to decrease or eliminate this bulging during the operation to provide the patient with the appropriate pain relief. In still a further use, the instrument is used to sense the three dimensional shape of the endplates and provide the user with this information. In one aspect, a processor evaluates the sensor signals and determines the appropriate geometric relationships based on the sensed data. An appropriate sized nucleus or other spacer may be selected based on the sensed endplate geometry. As a further aid to implant placement, in another aspect the sensor is used to detect the IAR for one or more disc spaces. The information from the handheld sensor is conveyed wirelessly, through a wired connection or through connection to a computer system through a data port such as a USB port. Similar devices are disclosed in United States patent application entitled SURGICAL INSTRUMENT TO ASSESS TISSUE CHARACTERISTICS, by Nycz et al. filed on even date as Ser. No. 11/356,643 which is incorporated herein by reference in its entirety.

Referring now to FIG. 6, there is shown a series of sensors 610, 620, and 630 placed adjacent the disc space between four adjacent vertebral bodies. Although sensors 610, 620 and 630 are shown as large rectangular shapes for the purpose of illustration, in one embodiment the sensor leads are less than 3 mm in width and approximately the same dimension in length. In one approach, the sensors 610, 620, and 630 are placed through a minimally invasive procedure, such as percutaneous placement via guided catheter or needle, in contact with or closely adjacent to the annulus tissues of the spinal segment. The sensors are joined to the respectively main housings 614, 624, and 634 by leads or connectors 612, 622 and 632, respectively. Connectors 612, 622, and 632 may include multiple sensors along their length. Further, main housing 624 may be used alone with sensors 610, 620 and 630 being directly connected to the main housing via connectors or wirelessly. In this manner, sensor signals are transmitted to the main housings positioned outside of the patient. Additionally, in one approach the connectors are used to extract the sensors after completion of the operation. In one aspect, sensors 610, 620 and 630 of the sensor provide information on the annulus tension. As explained above, if the disc space between V2 and V3 is the affected disc space being operated upon, the sensor will provide the surgeon with a "go" for further tension on the annulus as compared to the adjacent annulus or a "stop" when the appropriate tension has been reached matching or approximating the tension of the adjacent spinal levels. In another aspect, the sensor are positioned closer to the exiting nerve roots and provided data on the condition of the nerve roots and the location of potential sources of pain for the patient. Still further, in one diagnostic procedure, the sensors are left in position as the patient is moved through a series of predetermined motions. The sensors detect the LAR for each level and provide this data to the health care provider. The sensed IAR is then used by the surgeon to assist in proper placement of an interbody implant, such as a nucleus or artificial disc replacement device. During the operation, the sensor remains in place and indicates to the surgeon when the implant is in the sensed IAR position and provides a signal to maintain the position of the implant in the current position.

In addition to sensing the intradiscal environment prior to implant insertion, the instrument 500 is used after implant or graft positioning. In this embodiment, the instrument probes the disc space and indicates to the user the presence of any inappropriate materials. For instance, in a nucleus replacement or treatment procedure, bone particles from the endplates should not be present in the disc space. Alternatively, for fusion procedures the presence of nucleus material in or adjacent the graft material is contraindicated. Finally, in one aspect the instrument is inserted into the surgical wound. The instrument is energized and provides the user with an indication of any foreign materials remaining at the surgical site. For example, in this embodiment the instrument is programmed to detect surgical instruments remaining in the patient.

Figure 7:
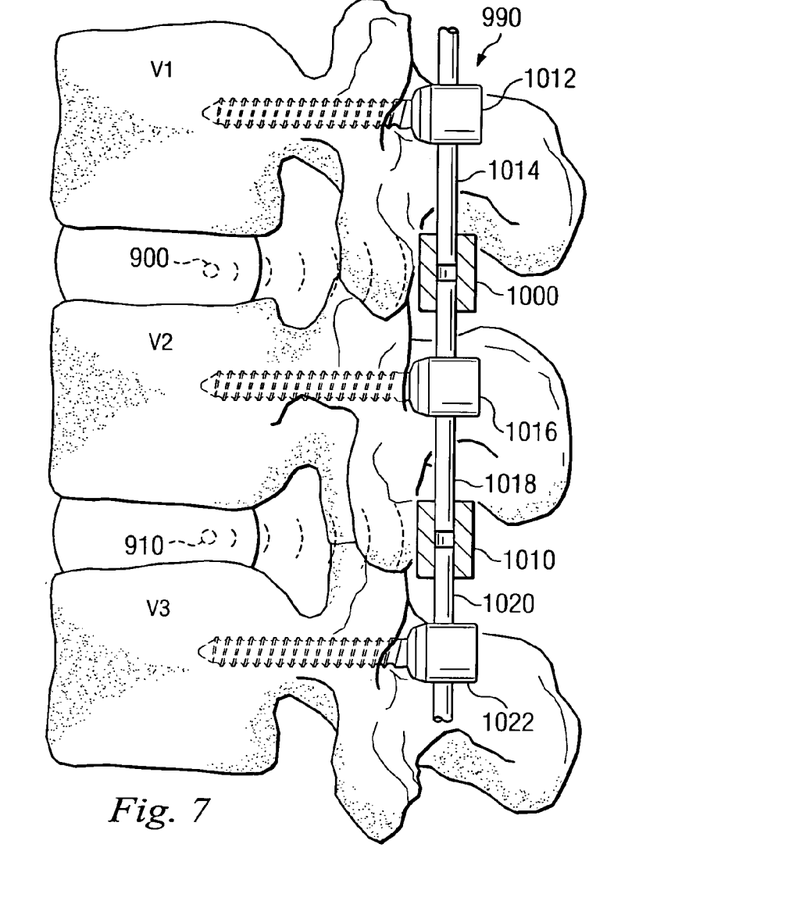
FIG. 7 is a side view of a spinal fixation system for dynamic stabilization in association with implantable sensors according to another aspect of the present invention.
Figure 8:
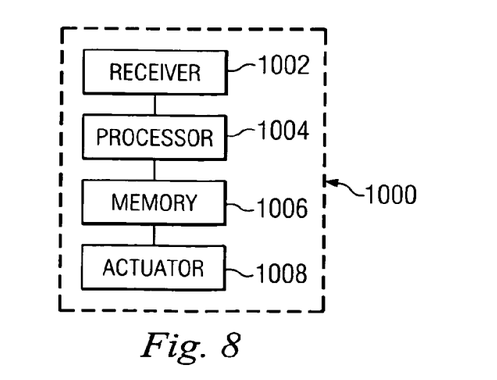
FIG. 8 is a schematic view of the dynamic controller of the stabilization system of FIG. 7.

Referring now to FIGS. 7-10, there is described use of sensors according to one aspect of the present invention in combination with controllable treatment devices. FIG. 7 illustrates a dynamic fixation system 990 extending between vertebrae V1, V2 and V3. Dynamic fixation system 990 includes a first bone fixation screw 1012 inserted into the pedicle of vertebra V1, a second bone fixation screw 1016 inserted into the pedicle of vertebra V2 and a third bone fixation screw 1022 inserted into the pedicle of vertebra V3. Each screw 1012, 1016 and 1020 are attached to a rod segment 1014, 1018 and 1020, respectively. A first dynamic actuator 1000 interconnects rod segments 1014 and 1018, and a second dynamic actuator 1010 interconnects rod segments 1018 and 1020. As shown in FIG. 8, dynamic actuators each included a receiver 1002 to receive data or control signals and a processor 1004 with associated memory 1006 to operate the actuator 1008. The dynamic actuators are operable to control the tension and/or compression on the adjacent rods. In a further aspect of one embodiment, dynamic actuators dampen movement between the rods and are controllable to stiffen or loosen the dampen force applied on the rods. In the illustrated embodiment, a sensor 900 is positioned in the space between vertebrae V1 and V2, and a similar sensor 910 is positioned in the space between vertebrae V2 and V3. In one aspect, the sensors sense pressure between the adjacent vertebrae and send a first signal indicating when pressure is above a first preset threshold level or send a second signal when pressure is below a second preset threshold level. As explained above, the threshold levels may be adjusted by self learning of the sensor or by external communications. If a first signal is sent by sensor 900, actuator 1000 will be controlled to increase compression on rods 1014 and 1018 to remove some of the load from the space between vertebrae V1 and V2. If a second signal is sent by sensor 900, then actuator 1000 decreases compression on the rods 1014 and 1018 such that more force is experienced across the disc space between vertebrae V1 and V2. It will be understood that in a fusion procedure bone has a tendency to grow in the presence of moderate compressive forces and atrophy in the absence of adequate pressure. In a fusion embodiment, sensor 910 and actuator 1010 operate to maintain the pressure across the disc space in the therapeutic range to promote bone growth. While a dynamic rod system has been shown for the purpose of illustration, it is contemplated that other types of dynamic load bearing systems will benefit from the disclosed combination, including but not limited to nucleus replacement devices, artificial discs, interbody spacers, anterior and posterior plating system, tethering systems, spinous process spacers, or facet spacers.

Figure 9:
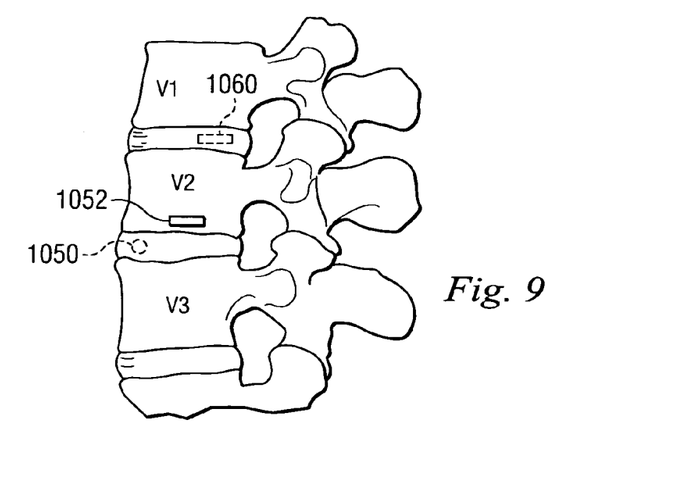
FIG. 9 is a side view of a sensor and a treatment compound dispenser in accordance with another aspect of the present invention.

Referring now to FIG. 9, there is shown a dynamic treatment system according to another aspect of the present invention. In a first embodiment, a sensor 1050 is disposed in the intradiscal space between vertebrae V2 and V3. Sensor 1050 includes the same features and capabilities as sensors 100 and 300 described above. Sensor 1050 is in communication with a therapeutic treatment reservoir 1052 disposed within vertebra V2. Sensor 1050 is programmed to sense the intradiscal environment as previously described above. In response to degradation of the disc space nutrients or physical structure of the spinal segment, sensor 1050 transmits a signal to the reservoir 1052. Based on the signal received, reservoir 1052 will release one or more treatment compounds to addressed the sensed deficiency in the disc space. As disclosed in U.S. Pat. No. 6,849,463 assigned to Microchips, incorporated herein by reference in its entirety, reservoir 1052 may include an array of selectively openable reservoirs and a processor for determine which reservoir should be opened. In a further aspect, the sensor and reservoirs are integrated into a single treatment unit 1060 shown disposed in the disc space between vertebrae V1 and V2. In this embodiment, the sensor is directly wired to the reservoir processor. Further, it is contemplated that one or more reservoirs may provide the treatment compound to the area outside the spinal segment. Alternatively or in addition to exterior treatment compounds, in one embodiment the reservoir treatment compounds are directed into the disc space or fed into the vertebral body adjacent the endplates such that they may enter the disc space through the natural nutrient channels, or man made channels, in the endplates to supply the treatment compound into the disc space. In another aspect, the sensor and reservoir are associated with other structures of the spinal segment such as the facets, annulus, nerve roots and spinal canal.

Examples of treatment compounds suitable for use with the present invention include but are not limited to a "biologically active component", with or without a "biological additive". A "biologically active component" includes but is not limited to anti-cytokines; cytokines; anti-interleukin-1 components (anti-IL-1); anti-TNF alpha; "growth factors"; LIM mineralization proteins; "stem cell material", autogenic chondrocytes; allogenic chondrocytes, such as those described in U.S. Patent Application Publication No. 2005/0196387, the entire disclosure of which is incorporated herein by reference; autogenic chondrocytes with retroviral viral vector or plasmid viral vector; allogenic chondrocytes with retroviral viral vector or plasmid viral vector; and fibroblasts. The acronym "LIM" is derived from the three genes in which the LIM domain was first described. The LIM domain is a cysteine-rich motif defined by 50-60 amino acids with the consensus sequence $CX_2CX_{16-23}HX_2CX_2CX_2CX_{16-21}CX_2(C/H/D)$, which contains two closely associated zinc-binding modules. LIM mineralization proteins include but are not limited to those described in U.S. Patent Application Publication No. 2003/0180266 A1, the disclosure of which is incorporated herein by reference. "Growth factors" include but are not limited to transforming growth factor (TGF)-beta 1, TGF-beta 2, TGF-beta 3, bone morphogenetic protein (BMP)-2, BMP-3, BMP-4, BMP-6, BMP-7, BMP-9, fibroblast growth factor (FGF), platelet derived growth factor (PDGF), insulin-like growth factor (ILGF); human endothelial cell growth factor (ECGF); epidermal growth factor (EGF); nerve growth factor (NGF); and vascular endothelial growth factor (VEGF). "Anti-IL-1" components include but are not limited to those described in U.S. Patent Application Publication Nos. 2003/0220283 and 2005/0260159, the entire disclosures of which are incorporated herein by reference. "Stem cell material" includes but is not limited to dedifferentiated stem cells, undifferentiated stem cells, and mesenchymal stem cells. "Stem cell material" also includes but is not limited to stem cells extracted from marrow, which may include lipo-derived stem cell material, and adipose-derived stem cell material, such as described in U.S. Publication Nos. 2004/0193274 and 2005/0118228, each of which is incorporated herein by reference. "Stem cell material" also includes but is not limited to stem cells derived from adipose tissue as described in U.S. Patent Application Publication Nos. 2003/0161816, 2004/0097867 and 2004/0106196, each of which is incorporated herein by reference.

A "biologically active component" also includes but is not limited to cartilage derived morphogenetic protein (CDMP); cartilage inducing factor (CIP); proteoglycans; hormones; and matrix metalloproteinases (MMP) inhibitors, which act to inhibit the activity of MMPs, to prevent the MMPs from degrading the extracellular matrix (ECM) produced by cells within the nucleus pulposus of the disc. Exemplary MMP inhibitors include but are not limited to tissue inhibitors, such as TIMP-1 and TIMP-2. Certain MMP inhibitors are also described in U.S. Patent Application Publication No. 2004/0228853, the entire disclosure of which is incorporated herein by reference.

A "biologically active component" also includes but is not limited to allogenic or xenogenic disc annulus material, such as described in U.S. Patent Application Publication No. 2005/0043801, the entire disclosure of which is incorporated herein by reference; biologic tissues, such as those described in U.S. Patent Application Publication No. 2003/0004574, the entire disclosure of which is incorporated herein by reference; an activated tissue graft, such as described in U.S. Patent Application Publication No. 2005/0136042, the entire disclosure of which is incorporated herein by reference; an engineered cell comprising a nucleic acid for encoding a protein or variant thereof, such as a BMP, a LIM mineralization protein, or an SMAD protein as described in U.S. Patent Application Publication Nos. 2003/0219423 and 2003/0228292, the entire disclosures of which are incorporated herein by reference; and a recombinant human bone morphogenetic protein, such as described in U.S. Patent Application Publication No. 2004/0024081, the entire disclosure of which is incorporated herein by reference.

As used herein, a "biological additive" includes but is not limited to "biomaterial carriers", "therapeutic agents", "liquids" and "lubricants."

"Biomaterial carriers" include but are not limited to collagen, gelatin, hyaluronic acid, fibrin, albumin, keratin, silk, elastin, glycosaminoglycans (GAGs), polyethylene glycol (PEG), polyethylene oxide (PEO), polyvinyl alcohol (PVA) hydrogel, polyvinyl pyrrolidone (PVP), co-polymers of PVA and PVP, other polysaccharides, platelet gel, peptides, carboxymethyl cellulose, and other modified starches and celluloses. Collagen includes but is not limited to collagen-based material, which may be autogenic, allogenic, xenogenic or of human-recombinant origin, such as the collagen-based material described in U.S. Patent Application Publication Nos. 2004/0054414 and 2004/0228901, the entire disclosures of which are incorporated herein by reference.

"Therapeutic agents" include but are not limited to nutrients, analgesics, antibiotics, anti-inflammatories, steroids, antiviricides, vitamins, amino acids and peptides. Nutrients include but are not limited to substances that promote disc cell survival, such as glucose and pH buffers, wherein the pH buffer provides a basic environment in the disc space, which preferably will be a pH of about 7.4. Analgesics include but are not limited to hydrophilic opoids, such as codeine, pro-drugs, morphine, hydromorphone, propoxyphene, hydrocodone, oxycodone, meperidine and methadone, and lipophilic opoids, such as fentanyl. Antibiotics include but are not limited to erythromycin, bacitracin, neomycin, penicillin, polymyxin B, tetracyclines, viomycin, chloromycetin and streptomycins, cefazolin, ampicillin, azactam, tobramycin, clindamycin and gentamycin.

"Liquids" include but are not limited to water, saline and radio-contrast media. Radio-contrast media includes but is not limited to barium sulfate, or a radio contrast dye, such as sodium diatrizoate (HYPAQUE™).

"Lubricants" include but are not limited to hyaluronic acid, a salt of hyaluronic acid, sodium hyaluronate, glucosaminoglycan, dermatan sulfate, heparin sulfate, chondroitin sulfate, keratin sulfate, synovial fluid, a component of synovial fluid, vitronectin and rooster comb hyaluronate.

A biological treatment may be introduced to an area of a vertebral column, such as a motion segment, by any method and in any form appropriate for such introduction. For example, the biological treatment can be injected, deposited, or applied, as a solution, a suspension, emulsion, paste, a particulate material, a fibrous material, a plug, a solid, porous, woven or non-woven material, or in a dehydrated or rehydrated state. Suitable forms for a biological treatment and suitable methods for injecting a biological treatment include those described in U.S. Patent Application Publication Nos.

2005/0267577, 2005/0031666, 2004/0054414, and 2004/0228901, each of which is incorporated herein by reference.

Figure 10:
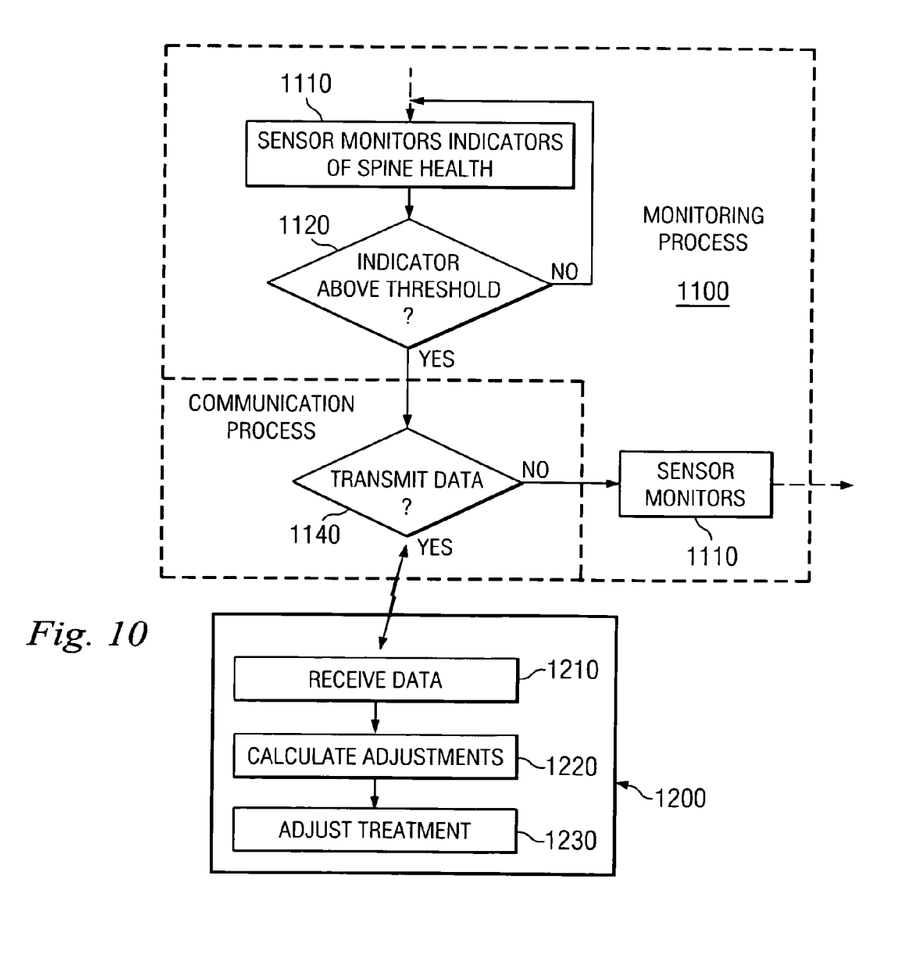
FIG. 10 is a flow chart illustrating use of an implantable sensor in combination with a treatment device.

In operation, the sensors and dynamic systems of FIGS. 7-10 operate as described in FIG. 10. In step 1110, the sensor monitors indicators of the spinal segment health. If the sensed indicator is not above the threshold, the sensor continues to monitor. If the sensed indicator is above a programmed threshold, in step 1120 the process continues onto the communication process in step 1140. If the sensor is unable to transmit the data, it will continue to monitor. If possible, the sensor will transmit its data to a dynamic treatment system designated as block 1200. The treatment system receives the data at step 1210 and adjusts the treatment at step 1230. The adjustment in treatment can be a mechanical adjustment of a mechanical system or control of a therapeutic treatment system. In a further aspect, the system provides the patient or health care provider with a recommendation of adjusting the treatment system. In this embodiment, the patient or health care provider considers the recommendation and instructs the dynamic treatment system to make an adjustment in response to the indicated sensor signal.

The foregoing sensor systems have application to various spinal procedures and conditions, including but not limited to, discectomy, neural decompression, bony defect repairs and bony fusions. The sensors may be placed temporarily or implanted within the disc space and disc nucleus to assure adequate debridement and site preparation for successive therapy and optimal outcomes. The sensors alone, or in combination with other systems, such as imaging systems, can interrogate the spinal segment to assess the optimal intradiscal pressures, nueral decompression, nutritional assay, annulus tension properties and other tissue characteristics. Further, the sensor can identify the annular wall dimensions, as well as weakness or rents in the annular wall. Further, the sensor can interrogate the implantation site to reduce the potential for foreign material in any procedure. For example, in one embodiment the sensor indicates to the surgeon whether sufficient debulking and debridement have been accomplished and whether any foreign bodies remain in the surgical site.

While the foregoing description has been made in reference to the spine, it is contemplated that the disclosed sensor has further applications throughout the body including the hip, knee, ankle, and jaw joints. Specifically, such disclosed sensors are useful to evaluate tissue density and detect changes to tissue throughout the body. It is contemplated that in another embodiment the sensor has a particular application with respect to detecting changes in bone density as it relates to osteoporosis. Further, in another embodiment the sensor is applied to detect tissue density changes with respect to tissue around fixation implants, joint implants, or any other type of implant. Moreover, an acoustic sensor may also be used to detect changes in viscosity. Thus, the sensor may be utilized to listen for changes in bodily systems and organs and alert healthcare professionals to any impending or potential problems. These examples of potential uses for the sensor are for example only and in no way limit the ways in which the current invention may be utilized.

Further, while the foregoing description has often described the external device as the means for displaying sensor data in human intelligible form, it is fully contemplated that the sensor itself may include components designed to display the data in a human intelligible form. For example, it is fully contemplated that the sensor may include a portion disposed subdermally that emits a visible signal for certain applications. Under one approach, the sensor might display a visible signal when it detects indicators indicative of conditions above the first threshold value. The sensor might also emit an audible sound in response to such indicators. In this sense, the sensor might act as an alarm mechanism for not only detecting potential problems but also alerting the patient and doctor to the potential problems. This can facilitate the early detection of problems. Under another approach, the sensor might display a different color visible signal depending on the indicators detected. For example, but without limitation, in the case of measuring tissue density the sensor might emit a greenish light if the indicators detected by the signal indicate density is within the normal range, a yellowish light if in a borderline range, or a red light if in a problematic range.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method for evaluating a condition of at least a portion of a spinal segment in a patient's body, comprising:
    providing a sensor having a sensing element and a communication circuit;
    implanting at least the sensing element into the patient's body;
    directing an energy signal toward the patient's spine;
    sensing a reflected energy signal at the sensing element to measure at least one nutrient opening in a portion of a spinal segment; and
    communicating the measured at least one nutrient opening to a user;
    wherein sensing the reflected energy signal provides a measurement of a plurality of nutrient openings in a vertebral endplate.

2. The method of claim 1, wherein said implanting includes positioning at least the sensing element into a disc space of the spinal segment located between upper and lower vertebral bodies.

3. The method of claim 1, wherein said implanting includes positioning at least the sensing element into the nucleus of the spinal segment.

4. The method of claim 1, wherein the measurement includes the size of the nutrient opening.

5. The method of claim 1, wherein the measurement includes the flow of material through the nutrient opening.

6. The method of claim 1, further including determining the distribution of the nutrient openings in the vertebral endplate.

7. The method of claim 1, further including determining the porosity of the nutrient openings in the vertebral endplate.

8. The method of claim 1, wherein said directing includes emitting an energy signal from said sensor.

9. The method of claim 1, wherein the communication circuit is utilized to communicate the measured at least one nutrient opening to a user.

10. A method for evaluating a condition of at least a portion of a spinal segment in a patient's body, comprising:
    providing a sensor having a sensing element and a communication circuit;
    implanting at least the sensing element into the patient's body directing an energy signal toward the patient's spine;

sensing a reflected energy signal at the sensing element to measure at least one nutrient opening in a portion of a spinal segment; and communicating the measured at least one nutrient opening to a user, wherein said sensing a reflected energy signal includes measuring at least one nutrient opening in a vertebral endplate.

11. The method of claim 10, wherein the communication circuit is utilized to communicate the measured at least one nutrient opening to a user.

12. The method of claim 10, wherein said implanting includes positioning at least the sensing element into a disc space of the spinal segment located between upper and lower vertebral bodies.

13. The method of claim 10, wherein said implanting includes positioning at least the sensing element into a nucleus of the spinal segment.

14. The method of claim 10, wherein the measured at least one nutrient opening communicated to the user includes the size of the nutrient opening.

15. The method of claim 10, wherein the measured at least one nutrient opening communicated to the user includes the flow of material through the nutrient opening.

16. The method of claim 10, wherein the sensing the reflected energy signal provides a measurement of a plurality of nutrient openings in the vertebral endplate.

17. The method of claim 16, further comprising determining the distribution of the plurality of nutrient openings in the vertebral endplate.

18. The method of claim 16, further comprising determining the porosity of the plurality of nutrient openings in the vertebral endplate.

19. The method of claim 10, wherein the directing an energy signal includes emitting an energy signal from the sensing element.

* * * * *